United States Patent
Oh et al.

(10) Patent No.: US 10,683,483 B2
(45) Date of Patent: Jun. 16, 2020

(54) MICROFABRICATED PLATFORM FOR MIMICKING THE LIVER ZONATION AND EVALUATING METHOD OF ZONAL TOXICITY USING THEREOF

(71) Applicant: Korea Research Institute of Chemical Technology, Daejeon (KR)

(72) Inventors: Jung-Hwa Oh, Daejeon (KR); Jaehwan Ahn, Daejeon (KR); Seokjoo Yoon, Daejeon (KR); Heeyoung Yang, Daejeon (KR); Jun-Ho Ahn, Daejeon (KR); Mi-Sun Choi, Daejeon (KR); Soojin Kim, Daejeon (KR); Se-Myo Park, Daejeon (KR); Hyoung-Yun Han, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/293,618

(22) Filed: Mar. 5, 2019

(65) Prior Publication Data
US 2019/0276799 A1 Sep. 12, 2019

(51) Int. Cl.
*C12N 5/071* (2010.01)
*C12N 5/00* (2006.01)

(52) U.S. Cl.
CPC .......... *C12N 5/067* (2013.01); *C12N 2501/33* (2013.01); *C12N 2501/39* (2013.01); *C12N 2501/999* (2013.01); *C12N 2533/54* (2013.01); *C12N 2533/74* (2013.01); *C12N 2533/80* (2013.01)

(58) Field of Classification Search
CPC .............. C12N 5/067; C12N 2501/999; C12N 5/0068; C12N 2533/76; C12N 2533/54; C12N 2533/74; C12N 2533/80; C12N 2501/727
See application file for complete search history.

(56) References Cited

FOREIGN PATENT DOCUMENTS

KR 10-2013-0138729 A 12/2013
KR 10-2014-0103914 A 8/2014
(Continued)

OTHER PUBLICATIONS

Regier et al., User-defined morphogen patterning for directing human cell fate stratification. Nature Scientific Reports, vol. 9 (Apr. 23, 2019) pp. 1-12. (Year: 2019).*
(Continued)

*Primary Examiner* — Kara D Johnson
(74) *Attorney, Agent, or Firm* — Lucas & Mercanti, LLP

(57) ABSTRACT

A microfabricated platform for mimicking the liver zonation and an evaluating method of zone-specific hepatotoxicity using the same is provided. The microfabricated platform for mimicking the liver zonation prepared according to the method of the present invention is divided into three zones of zone 1, zone 2 and zone 3 similarly to in vivo liver tissue and thus the zone-specific hepatotoxicity of a drug in the liver can be evaluated using the same. According to the present invention, the zone-specific hepatotoxicity results can be analyzed quantitatively by using image analysis, so that the platform of the present invention can be effectively used for in vitro screening of zone-specific hepatotoxicity.

10 Claims, 11 Drawing Sheets
(6 of 11 Drawing Sheet(s) Filed in Color)

(56) References Cited

FOREIGN PATENT DOCUMENTS

KR    10-2015-0103431 A    9/2015
WO       2016200340 A1    12/2016

OTHER PUBLICATIONS

Ahn et al., "Human three-dimensional in vitro model of hepatic zonation to predict zonal hepatotoxicity", Journal of Biological Engineering, 2019, vol. 13, No. 22, pp. 1-15.
Ise et al., "Analysis of cell viability and differential activity of mouse hepatocytes under 3D and 2D culture in agarose gel", Biotechnology Letters,1999, vol. 21, pp. 209-210.
Tran et al., "Hydrogel-based diffusion chip with Electric Cell-substrate Impedance Sensing (ECIS) integration for cell viability assay and drug toxicity screening", Biosensors and Bioelectronics, 2013, vol. 50, pp. 453-459.
Bhushan P. Mahadik et al., Micro uidic Generation of Gradient Hydrogels to Modulate Hernatopoietic Stem Cell Culture Environment, Advanced Healthcare Materials, 2014, vol. 3 Issue 3, pp. 449-458.
Vinay V. Abhyanka et al., A platform for assessing chemotactic migration within a spatiotemporally defined 3D microenvironment, Lab Chip., 2006, vol. 8 No. 9, pp. 1507-1515.
Bobak Mosadegh et al., Generation of Stable Complex Gradients Across Two-Dimensional Surfaces and Three-Dimensional Gels, Langmuir, 2007, Vol. 23, pp. 10910-10912.
Rolf Gebhardt et al., Liver zonation: Novel aspects of its regulation and its impact on homeostasis, World Journal of Gastroenterology, 2014, vol. 20 No. 26, pp. 8491-8504.
William J. McCarty et al., A Microfabricated Platform for Generating Physiologically-Relevant Hepatocyte Zonation, Scientific Reports, 2016, vol. 5, No. 6, 26868, (p. 1-10).

\* cited by examiner

MICROFABRICATED PLATFORM FOR MIMICKING THE LIVER ZONATION AND EVALUATING METHOD OF ZONAL TOXICITY USING THEREOF

CROSS-REFERENCE TO RELATED APPLICATION

This patent application claims priority of Korean Patent Application No. 10-2018-0027627, filed Mar. 8, 2018. The contents of which are incorporated herein by reference.

FIELD OF THE INVENTION

The present invention relates to a microfabricated platform for mimicking the liver zonation and an evaluating method of zone-specific hepatotoxicity using the same.

BACKGROUND OF THE INVENTION

Liver tissue consists of hexagonal unit structures called hepatic lobules. The hepatic lobule comprises hepatic vein (CV) in the center and portal triads (PT) in the periphery. In liver tissue, blood transports nutrients, hormones, waste products, and other signaling molecules from the portal triads to the hepatic vein through the pathway called sinusoid.

While blood is flowing through the sinusoid, liver cells are supplied nutritions via interaction with blood and exchange signaling molecules as well. So, those liver cells near the portal triads first consume such factors as nutritions, oxygen and hormones, and accordingly the concentration gradients of such factors are formed along the sinusoid. Due to the difference of in vivo environment, liver cells have functional heterogeneity according to the location where they belong, for example they have different functions such as ammonia detoxification, glucose and energy metabolism or external material metabolism.

In general, the regions to the hepatic vein are divided based on the portal triads as follows. The region around the portal triads is zone 1 (periportal area, PP), the region around the hepatic vein is zone 3 (perivenous area, PV), and the middle area is zone 2 (midzonal area). So, the zoning of hepatic lobule like the above is called liver zonation. Such division of the hepatic lobule is called liver zonation.

In the liver cells in zone 1 where oxygen-rich blood is flowing, such functions as gluconeogenesis, $\beta$-oxidation, cholesterol synthesis, ureogenesis, and the like are activated. These liver cells in zone 1 are susceptible to reactive oxygen, but display fast recovery. In the meantime, in the liver cells in zone 3 where oxygen-deficient blood is flowing, cytochrome P450 is highly activated so that not only drug metabolism is excellent but also such functions as lipogenesis, glycolysis, bile acid synthesis, and glutamine synthesis are activated. It is suggested thereby that the hepatic lobules are zoned and allotted with different functions to accomplish complicated liver functions simultaneously.

Studies on drug induced hepatotoxicity are an essential process to ensure drug safety in the development of new drugs. Various analysis methods have been developed for this purpose. For example, primary human hepatocytes are useful for the evaluation of hepatotoxicity in vitro by examining the expression of phase 1 and phase II enzymes. However, the primary human hepatocytes have disadvantages of unstable phenotypes in vitro, individual differences, difficulties in manipulation and high costs, because of which they have limitations in use. Thus, to overcome the problems above, various cell models capable of replacing the primary human hepatocytes have been studied. In relation to that, Korean Patent Publication No. 10-2015-0103431 describes a method for hepatotoxicity screening of immune based hepatotoxicity using human stem cell derived hepatocytes.

Although the hepatocyte model for toxicity evaluation has been dominantly studied to enhance the drug metabolism of hepatocytes themselves, the function of hepatic tissue has not been studied yet. However, studies of the hepatocyte model for toxicity evaluation have been mainly focused on the way to increase drug metabolism of hepatocytes themselves, and studies on the functions of the hepatic tissue according to the microenvironment of the hepatic tissue have not been progressed much.

Toxicity in hepatic tissue is induced under combined conditions. So, for the accurate evaluation and prediction of hepatotoxicity, it is necessary to develop a hepatotoxicity evaluation model reflecting not only the functions of hepatocytes themselves, but also the microenvironment of hepatic tissue. In particular, the drug metabolism environment differs according to the hepatic lobule zones, so that drug induced toxicity differs from the zones. Therefore, it is required to develop a microfabricated platform for mimicking the liver zonation reflecting such in vivo environment and an evaluating method of zone-specific hepatotoxicity using the same.

The present inventors tried to develop a cell model mimicking the in vivo environment of liver tissue. In the course of our study, the present inventors succeeded in preparing a microfabricated platform for mimicking the liver zonation by the processes of gelating hepatocytes by mixing the hepatocytes with a medium containing agarose in a tube, and forming a concentration gradient of CHIR in the gelated cells. And the present inventors further confirmed that the microfabricated platform for mimicking the liver zonation exhibited a difference in drug metabolism activity according to the zone and the result of the hepatotoxicity evaluation using the microfabricated platform for mimicking the liver zonation was consistent with the result of the hepatotoxicity evaluation using an animal model, leading to the completion of the present invention.

PRIOR ART REFERENCE (Patent Reference 1) Korean Patent Publication No. 10-2015-0103431

SUMMARY OF THE INVENTION

It is an object of the present invention to provide a method for producing a microfabricated platform for mimicking the liver zonation, and the microfabricated platform for mimicking the liver zonation prepared by the method above.

It is another object of the present invention to provide a screening method of hepatotoxicity using the microfabricated platform for mimicking the liver zonation above.

To achieve the above objects, the present invention provides a method for producing a microfabricated platform for mimicking the liver zonation comprising the steps of gelating hepatocytes by mixing the hepatocytes with a medium containing a gelatinizer in a tube, and forming a concentration gradient of a liver zonation factor or a material regulating the liver zonation factor in the gelated cells, followed by culture.

The present invention also provides a microfabricated platform for mimicking the liver zonation prepared by the method of the present invention.

Further, the present invention provides a screening method of zone-specific hepatotoxicity comprising the step of fragmenting the microfabricated platform for mimicking the liver zonation of the present invention to analyze cell viability.

The microfabricated platform for mimicking the liver zonation prepared according to the method of the present invention is divided into three zones of zone 1, zone 2 and zone 3 similarly to in vivo liver tissue and thus the zone-specific hepatotoxicity of a drug in the liver can be evaluated using the same. According to the present invention, the zone-specific hepatotoxicity results can be analyzed quantitatively by using image analysis, so that the platform of the present invention can be effectively used for in vitro screening of zone-specific hepatotoxicity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
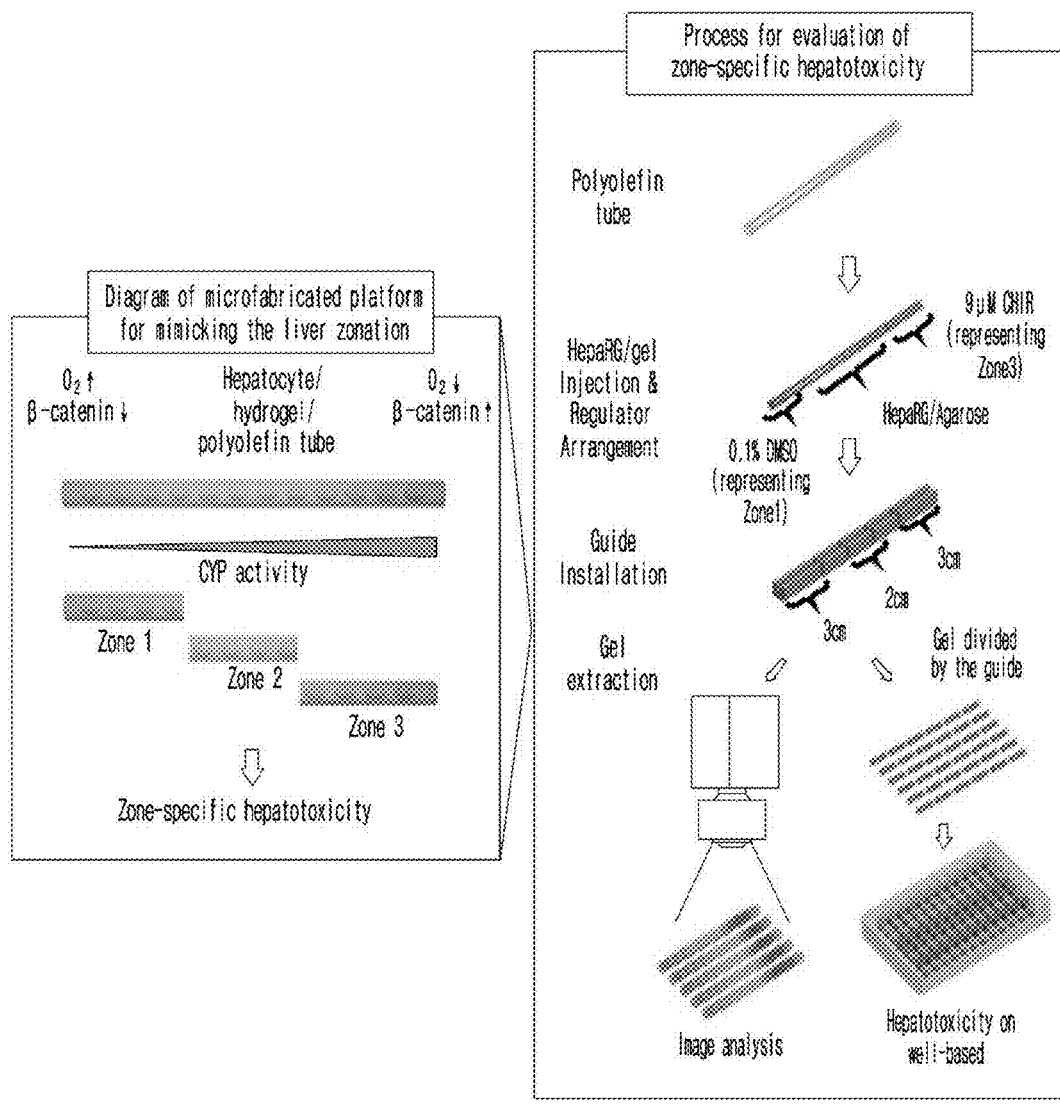
FIG. 1 is a set of a conceptual diagram illustrating the method for producing a microfabricated platform for mimicking the liver zonation according to the present invention and a schematic diagram illustrating the method for evaluating hepatotoxicity using the microfabricated platform for mimicking the liver zonation prepared by the method above.
Figure 2A:
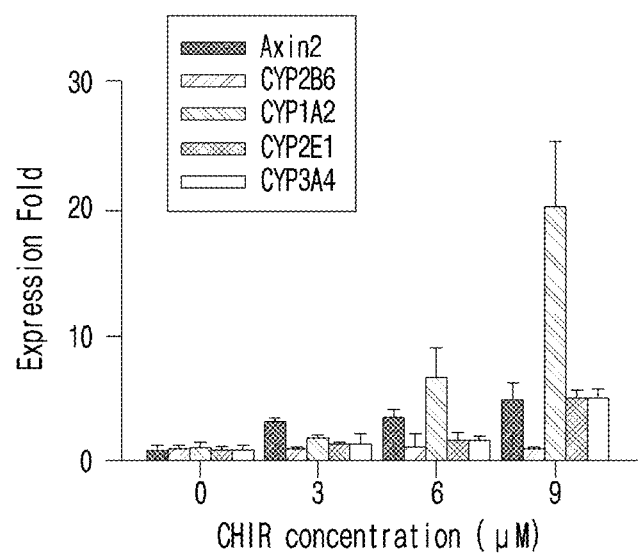
FIG. 2A is a graph illustrating the zone-specific expressions changes of CYP1A, CYP2E and CYP3A4 in the microfabricated platform for mimicking the liver zonation of the present invention.
Figure 2B:
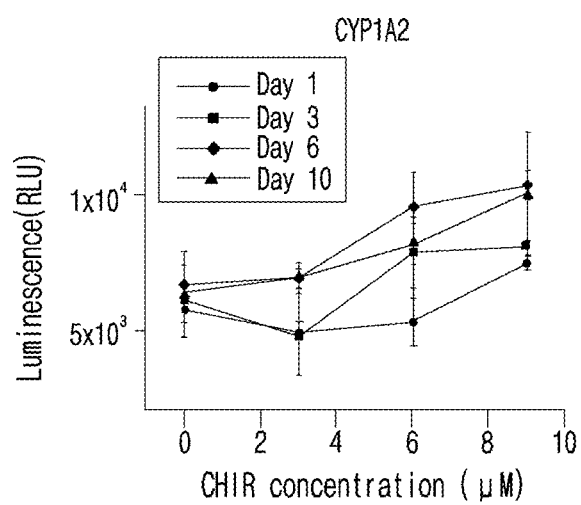
FIG. 2B is a graph illustrating the zone-specific activity changes of CYP1A in the microfabricated platform for mimicking the liver zonation of the present invention.
Figure 2C:
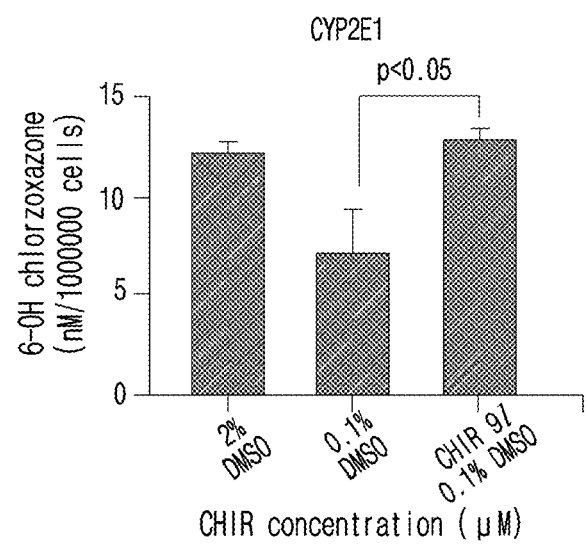
FIG. 2C is a graph illustrating the zone-specific activity changes of CYP2E in the microfabricated platform for mimicking the liver zonation of the present invention.
Figure 2D:
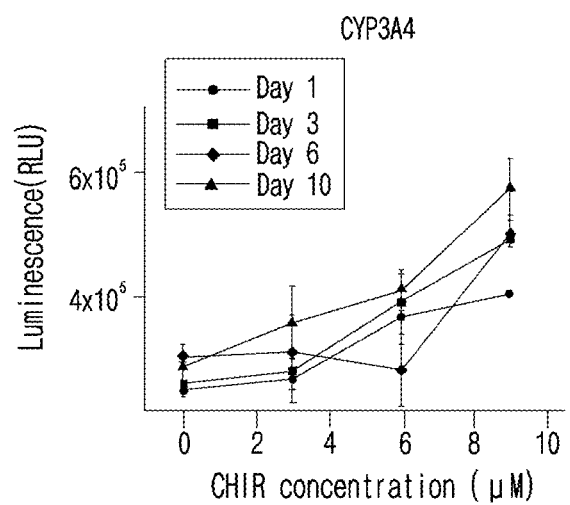
FIG. 2D is a graph illustrating the zone-specific activity changes of CYP3A4 in the microfabricated platform for mimicking the liver zonation of the present invention.

The present invention provides a method for producing a microfabricated platform for mimicking the liver zonation comprising the steps of gelating hepatocytes by mixing the hepatocytes with a medium containing a gelatinizer in a tube, and forming a concentration gradient of a liver zonation factor or a material regulating the liver zonation factor in the gelated cells, followed by culture.

In the method for producing a microfabricated platform for mimicking the liver zonation of the present invention, the hepatocytes can be any cells known to those in the art. The hepatocytes can be primary cultured hepatocytes, immortalized hepatocytes or hepatocytes differentiated from stem cells. Particularly, the hepatocytes can be one or more cell lines selected from the group consisting of HepG2, HepaRG, Hep3B and Huh7. The preferable density of the hepatocytes is $0.5 \times 10^2$ to $1 \times 10^{10}$ cell/ml, $1 \times 10^3$ to $10^{10}$ cell/ml, $1 \times 10^4$ to $10^{10}$ cell/ml, $1 \times 10^4$ to $10^7$ cell/ml, $0.5 \times 10^2$ to $10^9$ cell/ml, $0.5 \times 10^2$ to $10^8$ cell/ml, $0.5 \times 10^2$ to $10^7$ cell/ml, $0.5 \times 10^2$ to $10^6$ cell/ml, $1 \times 10^3$ to $10^8$ cell/ml or $1 \times 10^4$ to $10^7$ cell/ml.

The term "gelatinizer" used in this invention indicates a material that converts a fluid with liquidity into a solid, more precisely a material that can be included in a cell culture medium to prepare a solid type culture medium. The gelatinizer is not specifically limited unless it does not affect cell growth. For example, it can be agarose, collagen, gelatin, alginic acid, hyaluronic acid and MATRIGEL® (which is the trade name for a gelatinous protein mixture secreted by Engelbreth-Holm-Swarm (EHS) mouse sarcoma cells produced by Corning Life Sciences), etc. The gelatinizer can be added in an appropriate amount determined by to those in the art, and specifically can be contained at the concentration of 0.5 to 10% (w/v), 0.5 to 8% (w/v), 0.5 to 6% (w/v), 0.5 to 4% (w/v), 0.5 to 2% (w/v), 0.7 to 10% (w/v), 0.7 to 8% (w/v), 0.7 to 6% (w/v), 0.7 to 4% (w/v) or 0.7 to 2% (w/v).

Any culture medium known to be used for culturing hepatocytes can be selected as a culture medium containing the gelatinizer. Antibiotics, supplements and the like to be added to the culture medium can be appropriately selected and used according to need by those in the art.

In the production method of the present invention, the culture medium can contain the hepatocytes and the gelatinizer at the volume ratio of 1:0.1 to 10, 1:0.1 to 5, 1:0.1 to 4, 1:0.1 to 3, 1:0.1 to 2, 1:0.5 to 10, 1:0.5 to 5, 1:0.5 to 4, 1:0.5 to 3, or 1:0.5 to 2. The culture medium containing the cells and the gelatinizer at the volume ratio in the range above is loaded in a tube, followed by gelation. The tube can be made of at least one selected from the group consisting of such as.

The term used in this invention "liver zonation factor" indicates those factors known to be involved in liver zonation in vivo. The hepatocytes present in zone 1 are rich in oxygen, while the hepatocytes present in zone 3 are deficient in oxygen. So, the liver zonation factor can be a factor that can zone hepatocytes by increasing or decreasing oxygen. For example, the liver zonation factor can be one or more factors selected from the group consisting of Wnt/β-catenin signaling regulator, oxygen concentration gradient regulator, metabolic regulator, and hormone regulator. Particularly, the liver zonation factor can include β-catenin, oxygen, hydrogen peroxide, carbon dioxide, 3-methylcholanthrene, CYP inducer, CYP inhibitor and insulin.

The term used in this invention "material regulating the liver zonation factor" indicates a material that can regulate the liver zonation factor as described above. Particularly, the material regulating the liver zonation factor can include any material that is known to regulate the liver zonation factor as described above. For example, it can include CHIR, Wnt3 protein, oxygen, hydrogen peroxide, insulin and 3-methylcolanthrene, etc.

In the production method of the present invention, the liver zonation factor or the material regulating the liver zonation factor can be located at both ends of the gelated cells. The liver zonation factor or the material regulating the liver zonation factor located at both ends of the gelated cells diffuses into the gelated cells, thereby forms a concentration gradient. A microfabricated platform for mimicking the liver zonation can be produced by culturing the gelated cells wherein the concentration gradient has been formed by the liver zonation factor or the material regulating the liver zonation factor as such. The culture herein can be performed generally during the process of liver zonation and more specifically the duration of the culture can be 3 to 20 days, 3 to 15 days, 3 to 10 days, 3 to 8 days, 4 to 20 days, 4 to 15 days, 4 to 10 days, 4 to 8 days, 5 to 20 days, 5 to 15 days, 5 to 10 days, 5 to 8 days, 6 to 20 days, 6 to 15 days, 6 to 10 days, or 6 to 8 days.

In one embodiment of the present invention, the hepatocyte cell line HepaRG was mixed with a culture medium containing agarose, and the mixture was injected into a polyolefin tube and gelated. DMSO and CHIR were placed at both ends of the polyolefin tube containing the gelated hepatocytes in order to form a concentration gradient of CHIR in the gelated hepatocytes. A microfabricated platform for mimicking the liver zonation was produced by culturing the gelated hepatocytes for 7 days (see FIG. 1). The expressions and activities of CYP1A, CYP2E and CYP3A4 were increased in the hepatocytes exposed to high concentration of CHIR in the prepared microfabricated platform for mimicking the liver zonation (see FIGS. 2A to 2D).

Therefore, it was confirmed that a microfabricated platform for mimicking the liver zonation was able to be prepared by forming a concentration gradient of a factor inducing zonation in the gelated hepatocytes.

The present invention also provides a microfabricated platform for mimicking the liver zonation prepared by the production method of the invention.

The microfabricated platform for mimicking the liver zonation of the present invention can be prepared by the production method described above. As an example, the microfabricated platform for mimicking the liver zonation can be prepared by gelating hepatocytes in a tube, forming a concentration gradient of a liver zonation factor or a material regulating the liver zonation factor at both ends of the gelated hepatocytes, and culturing thereof. The gelatinizer is not specifically limited unless it does not affect cell growth. For example, it can be agarose, collagen, gelatin, alginic acid, hyaluronic acid and MATRIGEL® (which is the trade name for a gelatinous protein mixture secreted by Engelbreth-Holm-Swarm (EHS) mouse sarcoma cells produced by Corning Life Sciences), etc.

The liver zonation factor can be one or more factors selected from the group consisting of Wnt/β-catenin signaling regulator, oxygen concentration gradient regulator, metabolic regulator, and hormone regulator. In the meantime, the material regulating the liver zonation factor can be CHIR, Wnt3 protein, oxygen, hydrogen peroxide, insulin and 3-methylcolanthrene, etc.

The culture can be performed generally while the liver zonation progresses.

In one embodiment of the present invention, the hepatocyte cell line HepaRG was mixed with a culture medium containing agarose, and the mixture was injected into a polyolefin tube and gelated. DMSO and CHIR were placed at both ends of the polyolefin tube containing the gelated hepatocytes in order to form a concentration gradient of CHIR in the gelated hepatocytes. A microfabricated platform for mimicking the liver zonation was produced by culturing the gelated hepatocytes for 7 days (see FIG. 1). The expressions and activities of CYP1A, CYP2E and CYP3A4 were increased in the hepatocytes exposed to high concentration of CHIR in the prepared microfabricated platform for mimicking the liver zonation (see FIGS. 2A to 2D).

Therefore, it was confirmed that a microfabricated platform for mimicking the liver zonation was able to be prepared by forming a concentration gradient of a factor inducing zonation in the gelated hepatocytes.

In addition, the present invention provides a screening method of zone-specific hepatotoxicity comprising the step of fragmenting the microfabricated platform for mimicking the liver zonation of the present invention to analyze cell viability.

The microfabricated platform for mimicking the liver zonation of the present invention can be prepared by the production method described above. As an example, the microfabricated platform for mimicking the liver zonation can be prepared by gelating hepatocytes in a tube, forming a concentration gradient of a liver zonation factor or a material regulating the liver zonation factor at both ends of the gelated hepatocytes, and culturing thereof. The gelatinizer is not specifically limited unless it does not affect cell growth. For example, it can be agarose, collagen, gelatin, alginic acid, hyaluronic acid and MATRIGEL® (which is the trade name for a gelatinous protein mixture secreted by Engelbreth-Holm-Swarm (EHS) mouse sarcoma cells produced by Corning Life Sciences), etc.

The liver zonation factor can be one or more factors selected from the group consisting of Wnt/β-catenin signaling regulator, oxygen concentration gradient regulator, metabolic regulator, and hormone regulator. In the meantime, the material regulating the liver zonation factor can be CHIR, Wnt3 protein, oxygen, hydrogen peroxide, insulin and 3-methylcolanthrene, etc.

The culture can be performed generally while the liver zonation progresses.

The microfabricated platform for mimicking the liver zonation prepared by the production method of the present invention has the characteristics of being zoned in zone 1 to zone 3. So, the hepatocytes having different characteristics by zone can be obtained by segmenting the microfabricated platform for mimicking the liver zonation. The obtained hepatocytes can be distributed in a 96 well plate, followed by investigation of cell viability or hepatotoxicity related gene or protein, leading to the evaluation of hepatotoxicity. The investigation of cell viability or hepatotoxicity related gene or protein can be performed by a general method well known to those in the art. For example, the investigation of cell viability can be performed by using one or more reagents selected from the group consisting of MTT [3-(4,5-dimethylthiazole-2-yl)-2,5-diphenyltetrazolium bromide], XTT [sodium 3'-[1-[(phenylamino)-carbonyl]-3,4-tetrazolium]-bis(4-methoxy-6-nitro)benzene-sulphonic acid hydrate], MTS [3-(4,5-dimethylthiazole-2-yl)-5-(3-carboxymethoxyphenyl)-2-(4-sulfophenyl)-2H-tetrazolium)], WST (tetrazolium salt), NRU (neutral red uptake) and calcein AM. In the meantime, the investigation of hepatotoxicity related gene or protein can be performed by PCR, Western blotting, etc.

In one embodiment of the present invention, the present inventors produced a microfabricated platform for mimicking the liver zonation by forming a concentration gradient of CHIR in the hepatocytes injected into a polyolefin tube and gelated.

In the meantime, a microfabricated platform for mimicking the liver zonation was produced by using HepaRG cells fluorescent traceable using cell tracker deep red, which was treated with acetaminophen to evaluate hepatotoxicity. As a result, cells and CHIR were distributed regardless of exposure to acetaminophen, but the cells killed by acetaminophen were higher in the hepatocytes exposed to high concentration of CHIR (see FIGS. 3A to 3C).

The microfabricated platform for mimicking the liver zonation was treated with tamoxifen, which did not show zone-specific hepatotoxicity, and acetaminophen, which showed zone 3-specific hepatotoxicity, followed by evaluation of hepatotoxicity. As a result, tamoxifen induced hepatotoxicity regardless of zones, while acetaminophen induced zone 3-specific hepatotoxicity. These results were consistent with the experimental results using a rat animal model (see FIG. 4 and FIG. 5).

Figure 6:
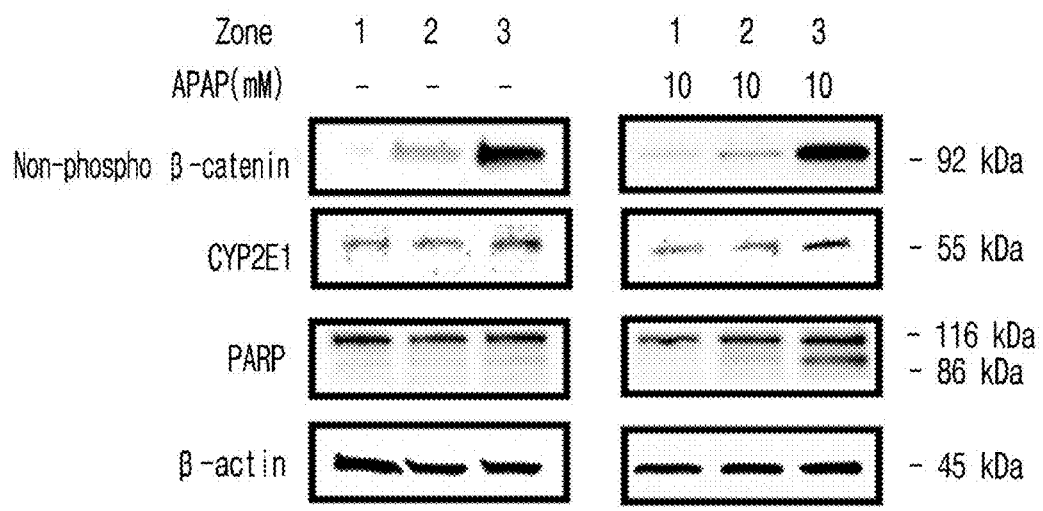
FIG. 6 is a set of photographs illustrating the zone-specific expression patterns of CYP2E1, PARP or β-catenin proteins after treating the microfabricated platform for mimicking the liver zonation of the present invention with acetaminophen.

In addition, the expression of cleaved PARP wherein the necrosis related protein was cleaved was increased in the hepatocytes displaying acetaminophen induced hepatotoxicity (see FIG. 6).

Therefore, it was confirmed that the microfabricated platform for mimicking the liver zonation prepared by the production method of the present invention can be used for screening hepatotoxic materials.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of Microfabricated Platform for Mimicking the Liver Zonation A mimetics of hepatic lobule, the structural unit constituting liver, was prepared in zoned form as follows (FIG. 1). At this time, CHIR [C6-[[2-[[4-(2,4-dichlorophenyl)-5-(5-methyl-1H-imidazol-2-yl)-2-pyrimidinyl]amino]ethyl]amino]-3-pyridinecarbonitrile)] increasing the amount of β-catenin, thereby increasing the drug metabolism efficiency and causing different drug responses according to the liver zone was used.

First, completely differentiated HepaRG cells (Biopredic Internation) were prepared by culturing the cells in the William's E culture medium (Gibco) supplemented with 0.1% DMSO, 1% L-glutamine, 1% penicillin/streptomycin, 10% fetal bovine serum (FBS), 5 µg/ml of insulin and 50 µM hydrocortisone. The prepared cells were suspended at the density of $1 \times 10^5$ cell/ml in the same William's E culture medium except that the medium contained 20% FBS instead of 10% FBS.

In the meantime, 20 mg of low melting temperature agarose was added to 1 ml of William's E culture medium supplemented with 2% L-glutamine, 2% penicillin/streptomycin, 10 µg/ml of insulin and 10 µM hydrocortisone, followed by melting at 90° C. for 2 hours to prepare a solid medium. At this time, low melting temperature agarose was used since generally used agarose has a high melting point so that cells might be damaged by heat in the process of recovering the cells. The suspended cells were added to an equal volume of the prepared medium and mixed. The mixture was injected into a polyolefin tube having a diameter of 3 mm and a length of 9 cm. At this time, the mixture was located in the center of the tube. The tube was fixed so as not to bend, followed by gelation at 37° C. HePaRG culture medium containing 0.1% DMSO (vehicle) and William's E culture medium containing 9 µM CHIR (β-catenin inhibitor) dissolved in 0.1% DMSO were located at both ends of the tube containing the gelated cells. That is, by placing 0.1% DMSO and 0.1% DMSO containing CHIR dissolved therein at both ends of the tube as described above, CHIR was allowed to migrate by diffusion. The tube was cultured at 37° C. for 7 days, resulting in the preparation of a microfabricated platform for mimicking the liver zonation.

Example 2: Investigation of Drug Metabolism Activity in HepaRG Cells Treated with CHIR, a Liver Zonation Factor The following experiment was performed to investigate whether or not the drug metabolism activity was different by zones in HepaRG cells treated with CHIR, a liver zonation factor.

First, the microfabricated platform for mimicking the liver zonation prepared in Example 1 was treated with luciferin-1A2 (Promega, USA) and luciferin-IPA (Promega, USA). Then, CYP1A and CYP3A4 drug metabolism enzymes were measured according to the manufacturer's protocol. In the meantime, to measure CYP2E, the microfabricated platform for mimicking the liver zonation was treated with 300 µM of CYP2E-specific chlorzoxazone and then 6-hydroxy chlorzoxazone, the metabolite, was measured by LC/MC to evaluate CYP2E.

As a result, as shown in FIG. 2, the expressions and activities of CYP1A, CYP2E and CYP3A4 were increased in the hepatocytes exposed to relatively high concentration of CHIR (FIGS. 2A to 2D).

Therefore, it was confirmed that the expressions and activities of CYP1A, CYP2E and CYP3A4 were increased by β-catenin because the expression of GSK-3B which is the enzyme that decomposes β-catenin in cells was inhibited by the CHIR treated to the microfabricated platform for mimicking the liver zonation. The increased drug metabolism enzyme activity accelerated in vivo drug metabolism so that a toxic metabolite was over-produced.

Experimental Example 1: Hepatotoxicity Evaluation Using Microfabricated Platform for Mimicking the Liver Zonation-(1)

The prepared microfabricated platform for mimicking the liver zonation was treated with acetaminophen, and hepatotoxicity was evaluated by the following method.

First, an impermeable fluorescent substance was formed in the inside of HepaRG cells by using cell tracker deep red fluorescent solution in order to trace the location of HepaRG cells. A microfabricated platform for mimicking the liver zonation was prepared by the same conditions and same manners as described in Example 1 by using the prepared HepaRG cells. The microfabricated platform for mimicking the liver zonation was cultured in a culture medium supplemented with 10 mM acetaminophen (APAP) for 48 hours. As a control, a culture medium without acetaminophen was used. Upon completion of the culture, the medium was removed and the dead cells were stained with EthD-1 (ethidium homodimer-1). Fluorescence in the stained cells were measured using chemi-Doc (Bio-Rad) at 650 to 657 nm, 302 nm and 625 to 650 nm, to examine the cells stained with deep red fluorescent solution, CHIR or EthD-1.

Figure 3A:
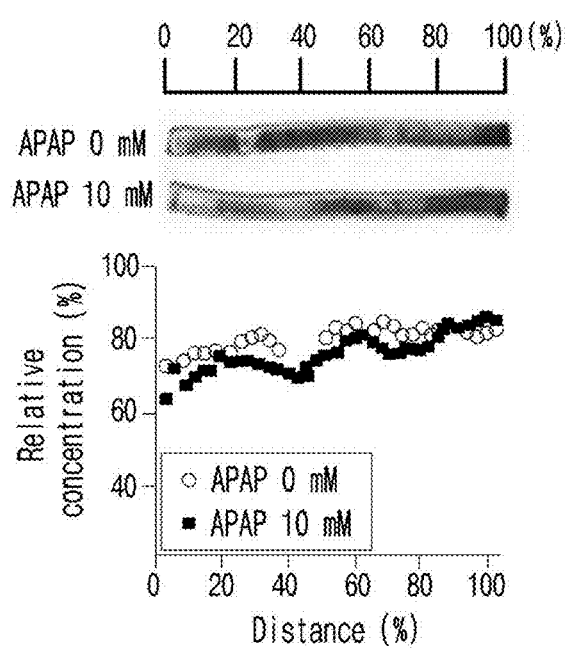
FIG. 3A is a set of graph and photograph illustrating the zone-specific hepatotoxicity investigated by cell staining (cell tracker deep red fluorescence) after treating the microfabricated platform for mimicking the liver zonation of the present invention with acetaminophen.
Figure 3B:
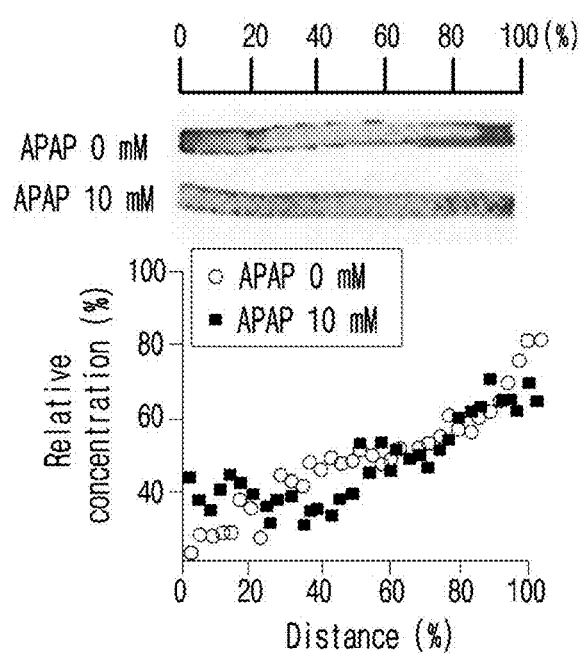
FIG. 3B is a set of graph and photograph illustrating the zone-specific hepatotoxicity investigated by cell staining CHIR after treating the microfabricated platform for mimicking the liver zonation of the present invention with acetaminophen.
Figure 3C:
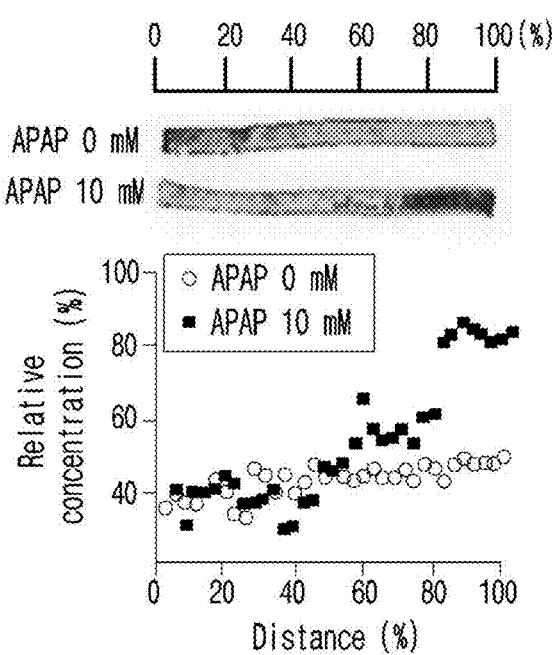
FIG. 3C is a set of graph and photograph illustrating the zone-specific hepatotoxicity investigated by apoptotic cell staining (EthD-1) after treating the microfabricated platform for mimicking the liver zonation of the present invention with acetaminophen.

As a result, as shown in FIG. 3A, the cell tracker deep red fluorescent solution was evenly distributed in cells regardless of exposure to acetaminophen. As shown in FIG. 3B, CHIR was also evenly distributed by diffusion. In the meantime, as shown in FIG. 3C, EthD-1 staining the dead cells showed high fluorescence intensity in those hepatocytes exposed to a relatively high concentration of CHIR (FIGS. 3A to 3C).

Therefore, from the results above, it was confirmed that the hepatic lobule mimetics was zoned by the treatment of CHIR and the acetaminophen induced toxicity was zone-specific.

Experimental Example 2: Hepatotoxicity Evaluation Using Microfabricated Platform for Mimicking the Liver Zonation-(2)

Acetaminophen and tamoxifen induced hepatotoxicity was evaluated by the following method using the prepared microfabricated platform for mimicking the liver zonation.

First, 6 tubes containing the microfabricated platform for mimicking the liver zonation prepared in Example 1 were divided into six equal pieces. The first piece of the microfabricated platform for mimicking the liver zonation obtained from each tube was placed in the first row of a 96-well plate, one per well. The second to sixth pieces were also placed on the second to sixth rows of a 96-well plate, respectively, in which a medium containing 0.1% DMSO was used as a culture medium. In the meantime, acetaminophen, the drug showing zone 3-specific hepatotoxicity, and tamoxifen showing no zone-specific hepatotoxicity were used as drugs to evaluate hepatotoxicity. Particularly, a crude liquid was prepared by dissolving acetaminophen in DMSO at the concentration of 2 M, and the crude liquid was diluted in the culture medium supplemented with 0.1% DMSO at the concentration of 12.5, 25, 50, 100 or 200 mM. In the meantime, a tamoxifen crude liquid was prepared by dissolving tamoxifen in DMSO at the concentration of 1 M, and the crude liquid was diluted in the culture medium supplemented with 0.1% DMSO at the concentration of 31.2, 62.5, 125, 250 or 500 µM. The diluted 200 mM acetaminophen and 500 µM tamoxifen were added to each well of the first row of a 96-well plate (200 µl/well), and the diluted 100 mM acetaminophen and 250 µM tamoxifen were added to each well of the second row of the 96-well plate (200 µl/well). In this manner, a medium without acetaminophen and tamoxifen was added to each well of the sixth row of the 96-well plate. The 96-well plate was cultured at 37° C. for 48 hours. Upon completion of the reaction, cells were washed with PBS and the absorbance of the cells was measured using cell counting kit-8 (Dojindo Molecular Technologies) according to the manufacturer's protocol. Cell viability was calculated from the measured absorbance value, and the results are shown in FIG. 4.

Figure 4:
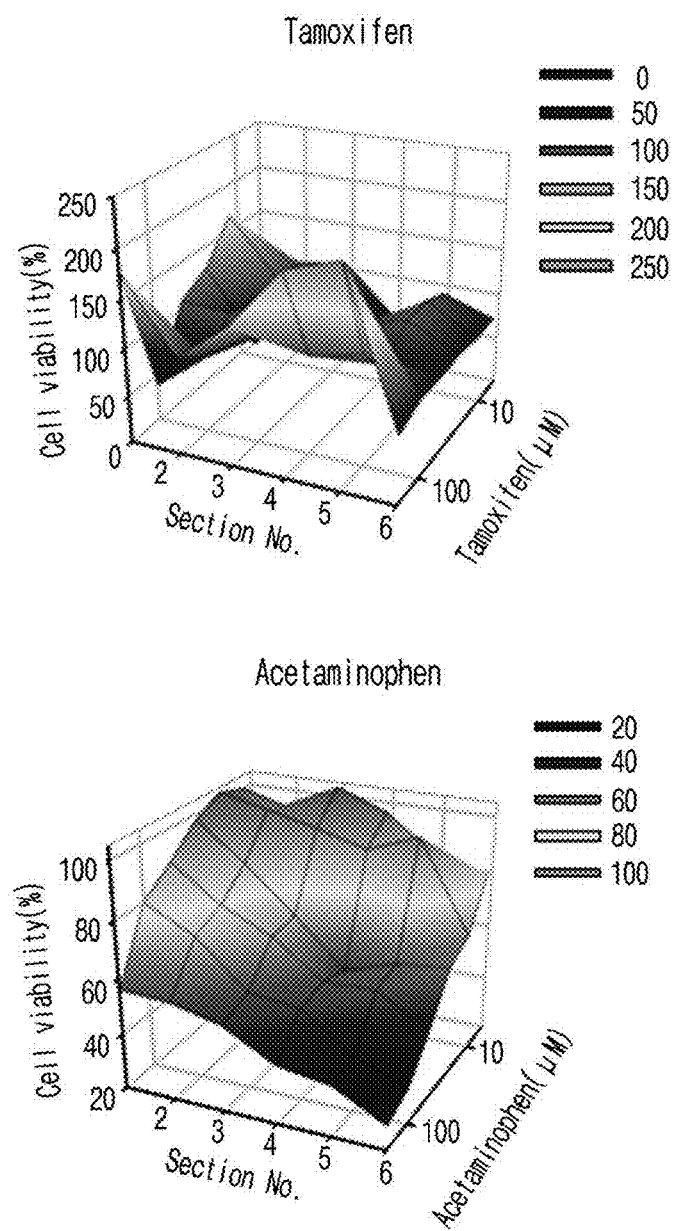
FIG. 4 is a set of graphs illustrating the zone-specific hepatotoxicity evaluated after treating the microfabricated platform for mimicking the liver zonation of the present invention with acetaminophen (A) or tamoxifen (B).

As shown in FIG. 4, the hepatocytes exposed to a relatively high concentration of CHIR in the course of a microfabricated platform for mimicking the liver zonation production process was more sensitive to the acetaminophen induced toxicity (FIG. 4A). In the meantime, tamoxifen demonstrated low cellular activity in the hepatocytes regardless of CHIR concentration exposed (FIG. 4B).

From the above results, it was confirmed that the metabolism of acetaminophen was significantly induced in the hepatocytes located in the region where CHIR was distributed at a high concentration and as a result a toxic intermediate metabolite was generated in a large amount, so that the hepatocytes located in the region where CHIR was distributed at a high concentration were more sensitive to cytotoxicity than the hepatocytes in a region where CHIR was distributed at a low concentration.

Experimental Example 3: Hepatotoxicity Evaluation Using Microfabricated Platform for Mimicking the Liver Zonation-(3)

The following experiment was performed in order to compare the results of the hepatotoxicity evaluation using the microfabricated platform for mimicking the liver zonation above with the results obtained from the experiment using an animal model.

First, Sprague Dawley rats were orally administered with 1,000 mg/kg of acetaminophen or 60 mg/kg of tamoxifen once a day for 3 days. After the administration, the animals were sacrificed, from which the liver tissues were obtained. The obtained liver tissues were stained with H&E, followed by observation under a microscope. The results are shown in FIG. 5.

Figure 5:
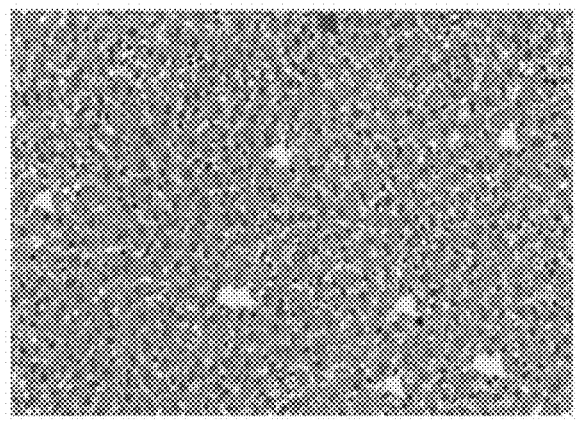
FIG. 5 is a set of photographs illustrating the hepatotoxicity in liver tissue of a rat model treated with acetaminophen or tamoxifen (yellow: increase of mitosis, blue: necrosis, and green: inflammatory cell infiltration).
Figure 5:
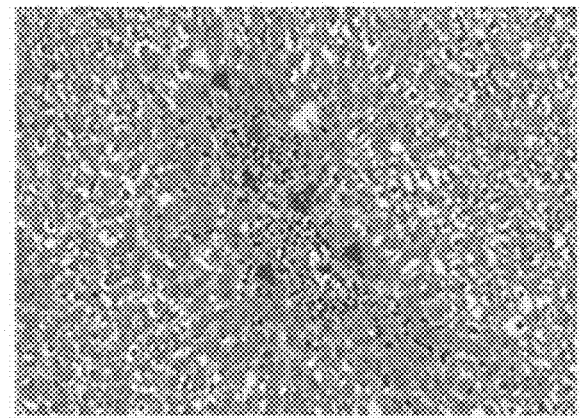

As shown in FIG. 5, consistently with the results of the experiment above using the microfabricated platform for mimicking the liver zonation, acetaminophen induced toxicity increased mitosis (yellow triangle), necrosis (blue triangle) and inflammatory cell infiltration (green triangle) in the central vein of the liver (zone 3). In the meantime, tamoxifen induced hepatocellular hypertrophy in the liver regardless of zones (FIG. 5).

Therefore, it was confirmed that the microfabricated platform for mimicking the liver zonation prepared in this invention displayed zone-specific hepatotoxicity as in the animal model.

Experimental Example 3: Investigation of Protein Expression Changes in Microfabricated Platform for Mimicking the Liver Zonation The changes in the expression of hepatotoxicity related proteins in the microfabricated platform for mimicking the liver zonation induced with toxicity or not induced with toxicity were investigated by Western blotting.

Particularly, 3 tubes containing the microfabricated platform for mimicking the liver zonation prepared in Example 1 were divided into three equal pieces. The first piece of the microfabricated platform for mimicking the liver zonation obtained from each tube was placed in the first row of a 6-well plate, one per well. The second and third pieces were also placed on the second and third rows of a 6-well plate, respectively, in which a medium containing 0.1% DMSO was used as a culture medium. Acetaminophen was added thereto at the concentration of 10 mM, followed by culture for 48 hours. Upon completion of the culture, 5×RIPA buffer and 4× sample buffer were added to each well, followed by heating at 90° C. for 10 minutes to melt agarose gel. 3 to 5 units of agarase were added thereto, followed by stirring at 42° C. for 90 minutes. After the stirring, the obtained protein was loaded on a 10-well gradient gel, followed by electrophoresis at 80 V for approximately two hours. The electrophoresed protein was transferred onto a cellulose sheet and the cellulose sheet was pretreated with 10% skim milk. As a primary antibody, β-catenin, CYP2E1 or PARP antibody was added thereto, followed by reaction. Then, the protein expression was confirmed.

As a result, as shown in FIG. 6, the expressions of β-catenin and CYP2E1 protein were increased in the hepatocytes located in zone 3 compared to the hepatocytes located in zone 1 by liver zonation. In the microfabricated platform for mimicking the liver zonation treated with acetaminophen, cleaved PARP, a necrosis related protein, was detected in the hepatocytes present in zone 3 (FIG. 6).

Therefore, it was confirmed that the microfabricated platform for mimicking the liver zonation according to the present invention can be effectively used for the evaluation of zone-specific hepatotoxicity.

The invention claimed is:

1. A method for producing a microfabricated platform for mimicking the liver zonation comprising the following steps:
   1) gelating hepatocytes by mixing the hepatocytes with a medium containing a gelatinizer in a tube; and
   2) forming a concentration gradient of CHIR99021 6-[[2-[[4-(2,4-Dichlorophenyl)-5-(5-methyl-1H-imidazol-2-yl)-2-pyrimidinyl]amino]ethyl]amino]-3-pyridinecarbonitrile] in the gelated cells of step 1), followed by culture.

2. The method for producing a microfabricated platform for mimicking the liver zonation according to claim 1, wherein the gelatinizer is included at the concentration of 0.5 to 10% (w/v).

3. The method for producing a microfabricated platform for mimicking the liver zonation according to claim 1, wherein the density of the hepatocytes of step 1) is $0.5 \times 10^2$ to $1 \times 10^{10}$ cell/ml.

4. The method for producing a microfabricated platform for mimicking the liver zonation according to claim 1, wherein the culture medium contains the cells and the gelatinizer at the volume ratio of 1:0.1 to 10.

5. The method for producing a microfabricated platform for mimicking the liver zonation according to claim 1, wherein the gelatinizer is one or more selected from the group consisting of agarose, collagen, gelatin, alginic acid, and hyaluronic acid.

6. The method for producing a microfabricated platform for mimicking the liver zonation according to claim 1, wherein the concentration gradient is formed by diffusing CHIR99021 [6-[[2-[[4-(2,4-Dichlorophenyl)-5-(5-methyl-1H-imidazol-2-yl)-2-pyrimidinyl]amino]ethyl]amino]-3-pyridinecarbonitrile] at both ends of the tube.

7. The method for producing a microfabricated platform for mimicking the liver zonation according to claim 1, wherein the culture is performed for 3 to 20 days.

8. The method for producing a microfabricated platform for mimicking the liver zonation according to claim 1, wherein the tube is made of one or more materials selected from the group consisting of polyolefin, polydimethylsiloxane, silicone, glass and latex.

9. A microfabricated platform for mimicking the liver zonation prepared by the method of claim 1.

10. A method for screening of zone-specific hepatotoxicity comprising:
    fragmenting the microfabricated platform for mimicking the liver zonation of claim 9; and
    analyzing cell viability.

* * * * *